(12) United States Patent
Tortelli et al.

(10) Patent No.: US 9,447,007 B2
(45) Date of Patent: Sep. 20, 2016

(54) PROCESS FOR PRODUCING FLUORINATED ORGANIC COMPOUNDS

(75) Inventors: Vito Tortelli, Milan (IT); Marco Galimberti, Bollate (IT); Cristiano Monzani, Trezzo Sull'Adda (IT); Piero Gavezotti, Milan (IT)

(73) Assignee: SOLVAY SPECIALTY POLYMERS ITALY S.P.A., Bollate (Milano) (IT)

( * ) Notice: Subject to any disclaimer, the term of this patent is extended or adjusted under 35 U.S.C. 154(b) by 117 days.

(21) Appl. No.: 13/993,154

(22) PCT Filed: Dec. 16, 2011

(86) PCT No.: PCT/EP2011/073138
§ 371 (c)(1),
(2), (4) Date: Jun. 11, 2013

(87) PCT Pub. No.: WO2012/084745
PCT Pub. Date: Jun. 28, 2012

(65) Prior Publication Data
US 2013/0256588 A1 Oct. 3, 2013

(30) Foreign Application Priority Data

Dec. 21, 2010 (EP) .................................. 10196096

(51) Int. Cl.
| | |
|---|---|
| *C07C 41/22* | (2006.01) |
| *C07C 41/48* | (2006.01) |
| *C08G 65/00* | (2006.01) |
| *C08G 65/323* | (2006.01) |
| *C09K 5/00* | (2006.01) |

(52) U.S. Cl.
CPC ............... *C07C 41/22* (2013.01); *C07C 41/48* (2013.01); *C08G 65/007* (2013.01); *C08G 65/3236* (2013.01); *C09K 5/00* (2013.01)

(58) Field of Classification Search
CPC .......... C07C 43/00; C07C 17/00; C11D 7/28
See application file for complete search history.

(56) References Cited

U.S. PATENT DOCUMENTS

| | | | |
|---|---|---|---|
| 3,665,041 A | 5/1972 | Sianesi et al. | |
| 4,845,268 A | 7/1989 | Ohsaka et al. | |
| 4,960,951 A | 10/1990 | Nappa et al. | |
| 5,093,432 A | 3/1992 | Bierschenk et al. | |
| 6,149,980 A | 11/2000 | Behr et al. | |
| 6,753,301 B2 | 6/2004 | Howell et al. | |
| 7,691,282 B2 * | 4/2010 | Flynn .................. | C07C 43/126 134/42 |
| 8,791,254 B2 | 7/2014 | Vitcak .................. | C07D 309/10 544/174 |
| 2003/0157800 A1 | 8/2003 | Ohno et al. | |
| 2003/0215735 A1* | 11/2003 | Wheland .............. | C08F 214/186 430/270.1 |
| 2005/0277052 A1* | 12/2005 | Feiring ................. | C08F 214/18 430/270.1 |
| 2007/0207413 A1* | 9/2007 | Crawford ............... | C07C 33/44 430/311 |
| 2008/0245509 A1* | 10/2008 | Costello ................ | C09K 5/10 165/104.19 |
| 2010/0028784 A1* | 2/2010 | Pham .................... | H01M 6/164 429/332 |
| 2011/0215273 A1* | 9/2011 | Uenveren ............. | C07C 17/206 252/78.1 |
| 2013/0256588 A1* | 10/2013 | Tortelli ................. | C07C 41/22 252/78.1 |

FOREIGN PATENT DOCUMENTS

| | | |
|---|---|---|
| EP | 0344935 A2 | 12/1989 |
| WO | WO 9640834 A1 | 12/1996 |
| WO | WO 02066408 A2 | 8/2002 |
| WO | WO 2005110957 A2 | 11/2005 |
| WO | WO 2006081282 A1 | 8/2006 |

OTHER PUBLICATIONS

RD 169083 A, May 10, 1978, Anonymous.
Sandford, G.—"Perfluoroalkanes", 2003, Tetrahedron, vol. 59, Elsevier Science Ltd., pp. 437-454; 18 pgs.
Chambers, R.D., et al—"Elemental fluorine. Part 11 [1]. Fluorination of modified ethers and polyethers", 2000, Journal of Fluorine Chemistry, vol. 101, Elsevier Science S.A., pp. 97-105; 9 pgs.
Sievert, A.C., et al—"Synthesis of perfluorinated ethers by an improved solution phase direct fluorination process", 1991, Journal of Fluorine Chemistry, vol. 53, Elsevier Sequoia, Lausanne, pp. 397-417; 21 pgs; XP-002019234.
Berenblit, V.V., et al—"The Nature of the products of the electrochemical fluorination of ethers of ethylene glycol", 1974, translated from Zhurnal Organicheskoi Khimii, vol. 10, Issue No. 10, pp. 2031-2035—translation in English pp. 2048-2051; 4 pgs.
Murata, J., et al—"Selective synthesis of fluorinated ethers by addition reaction of alcohols to fluorinated olefins in water", 2002, Green Chemistry, vol. 4, Issue No. 1, The Royal Society of Chemistry, pp. 60-63; 4 pgs.
Furin, G.G., "Synthesis and use of fluorine-containing simple ethers based on perfluoro olefins", 2006, Khimiya v Interesakh Ustoichivogo Razvitiya, vol. 14, Issue No. 4, pp. 327-342; 17 pgs, Includes abstract in English.
Furin, G.G., "Synthesis and Application of Fluorine-Containing Ethers Based on Perfluoroolefins", 2006, Chemistry for Sustainable Development, vol. 14, pp. 303-318; 16 pgs.

* cited by examiner

*Primary Examiner* — Gregory Webb

(57) ABSTRACT

A process for fluorinating hydrocarbon compounds, which comprises:
A. providing a compound selected from the group consisting of straight-chain, branched-chain and cyclic alkanes, straight-chain, branched-chain and cyclic ethers, said compound comprising at least one carbon-hydrogen bond and being free from —C(O)— functional groups;
B. reacting said compound with fluorine in the presence of at least one (per)haloolefin comprising at least one carbon-carbon double bond and having at least one fluorine or chlorine atom on either one of the carbon atoms of said double bond, to obtain a compound wherein at least one carbon-hydrogen bond has been replaced by a carbon-fluorine bond. Compositions of partially fluorinated compounds obtained with the process are also disclosed.

15 Claims, No Drawings

PROCESS FOR PRODUCING FLUORINATED ORGANIC COMPOUNDS

CROSS-REFERENCE TO RELATED APPLICATIONS

This application is a U.S. national stage entry under 35 U.S.C. §371 of International Application No. PCT/EP2011/073138 filed Dec. 16, 2011, which claims priority to European application No. 10196096.1 filed Dec. 21, 2010, the whole content of this application being incorporated herein by reference for all purposes.

TECHNICAL FIELD

The invention relates to a process for fluorinating hydrocarbon compounds comprising at least one carbon-hydrogen bond, in particular compounds selected among the group consisting of alkanes and ethers.

BACKGROUND ART

Various methods of converting, part or all of, the C—H bonds in a hydrocarbon compound are known. Examples include a method of using cobalt trifluoride, a method of conducting fluorination reaction by using as a fluorine source hydrogen fluoride generated in electrolysis in an electrolytic bath (generally referred to as electrolytic fluorination) and a method of conducting fluorination directly in the liquid phase by using fluorine gas (generally referred to as direct fluorination) as disclosed in SANDFORD, G. Perfluoroalkanes. *Tetrahedron:Tetrahedron:* 0040-4020. 2003, vol. 59, p. 437-454. and in CHAMBERS, R. D., et al. Elemental fluorine. Part 11 [1]. Fluorination of modified ethers and polyethers. *Journal of Fluorine Chem.* 2000, vol. 101, p. 97-105.

The fluorination method using cobalt trifluoride and the electrolytic fluorination method may cause isomerization, cleavage of the main chain and/or recombination reactions thus reducing the yield in the desired end product.

On the other hand an issue encountered in the direct fluorination with fluorine is the increasing difficulty in the hydrogen substitution with increasing fluorine content in the compound. With increasing numbers of neighbouring fluorine atoms C—H bonds become more electron deficient and consequently hydrogen-abstraction by electrophilic fluorine atoms becomes more difficult. To prevent carbon-carbon bond cleavage during a fluorination reaction the heat generated in the reaction has to be rapidly dissipated. Accordingly, fluorine is generally provided under dilute conditions, typically diluted with an inert gas. Thus, in the initial stages of the fluorination reaction dilute fluorine is used and the reaction system is cooled. However, as the fluorination reaction progresses and fluorination becomes increasingly difficult the concentration of fluorine has to be increased and the temperature generally raised. The use of UV light to activate the final stages of the fluorination reaction has been disclosed for instance in EP 344935 A (DU PONT DE NEMOURS AND CO.) Jun. 12, 1989 and in U.S. Pat. No. 4,960,951 (DU PONT DE NEMOURS AND CO.) Feb. 10, 1990 both directed to the preparation of perfluorinated polyethers with elemental fluorine.

Addition of aromatic compounds, such as benzene, hexafluorobenzene or toluene, to promote the final stages of the perfluorination reaction of hydrogenated ethers and polyethers with molecular fluorine has been disclosed for instance in U.S. Pat. No. 5,093,432 (EXFLUOR RESEARCH CORPORATION) Mar. 3, 1992 which relates to a process for the liquid phase fluorination of ethers and polyethers with fluorine in a perhalogenated liquid medium. The use of trichloroethylene is mentioned as a cosolvent to improve the solubility of the hydrogenated starting material in the perhalogenated liquid medium.

However, the above described processes have the drawback that, to obtain a fully fluorinated product, a large excess of fluorine over the stoichiometrically required quantity, is needed. The need to provide a large excess of fluorine over the stoichiometrically required quantity makes it difficult to control the degree of hydrogen substitution when only partial fluorination of the starting compound is required.

There is thus still a need in the art for a process for the fluorination, full or partial, of hydrocarbon compounds, in particular alkanes and ethers, comprising a fluorination step that may be carried out under mild conditions and providing high yields. Additionally it would be highly advantageous to have a process wherein the substitution of C—H bonds with C—F bonds proceeds in a stoichiometric manner and with complete conversion of the fluorine so that the degree of fluorine substitution can be controlled by controlling the amount of fluorine fed to the reaction system.

DISCLOSURE OF INVENTION

It is thus an object of the present invention to provide a process for the full or partial fluorination of hydrocarbon compounds free from functional —C(O)— groups, which advantageously proceeds with high yields. It is also an additional object of the present invention to provide a fluorination process that proceeds with the stoichiometric substitution of the hydrogen atoms in the starting compound without the need to operate with high excess of fluorine, so that well defined mixture of products deriving from the partial fluorination reaction of the starting material can be obtained by controlling the amount of fluorine fed to the system.

The process of the invention thus comprises:
  A. providing a compound selected from the group consisting of straight-chain, branched-chain and cyclic alkanes, straight-chain, branched-chain and cyclic ethers comprising at least one carbon-hydrogen bond, said compound being free from —C(O)— functional groups;
  B. reacting said compound with fluorine in the presence of at least one (per)haloolefin comprising at least one carbon-carbon double bond and having at least one fluorine or chlorine atom on either one of the carbon atoms of said double bond, to obtain a compound wherein at least one carbon-hydrogen bond has been replaced by a carbon-fluorine bond; the amount of (per)haloolefin being from 0.1 to 30 mol % with respect to the hydrogen atoms contained in the hydrocarbon compound.

The presence of a (per)haloolefin in step B of the process, as above described, allows to carry out the process according to the invention under mild conditions, so that no undesired decomposition of the reagents occurs. Additionally, a very high conversion of the hydrocarbon compound as well as a remarkable selectivity in the formation of the desired partially or fully fluorinated product are obtained. Furthermore, a large excess of fluorine is not required to achieve substitution of C—H bonds, conversion of this latter being very high in the present process. Without intending to limit the invention to a particular theory, it is believed that the (per)haloolefin acts as radical initiator in the reaction of fluorine with the hydrocarbon compound and accordingly enables to achieve outstanding reaction rates in the fluorination step.

The expression "(per)haloolefin comprising at least one carbon-carbon double bond and having at least one fluorine or chlorine atom on either one of the carbon atoms of said double bond" is intended to encompass fluoroolefins, chloroolefins, and fluorochloroolefins, these compounds possibly comprising one or more heteroatom different from Cl and F, in particular oxygen. Preferably the (per)haloolefin is a perfluoroolefin.

Suitable starting material to be used in the inventive fluorination process is a hydrocarbon compound selected from the group consisting of straight-chain, branched-chain and cyclic alkanes, straight-chain, branched-chain and cyclic ethers comprising at least one carbon-hydrogen bond, said compound being free from —C(O)— functional groups. The expression "—C(O)— functional groups" is intended to refer to any functional group comprising carbon-oxygen double bonds and thus it is intended to encompass, but is not limited to, carboxylic acid functional groups as well as carboxylic acid derivatives, including acyl halides, amides, esters, ketones, aldehyde functional groups. It has been observed that the presence of —C(O)— functional groups, in particular —C(O)F functional groups, may sometimes result is the formation of products deriving from the addition of the —C(O)F group to the carbon-carbon double bond of the olefin.

The starting hydrocarbon compound may be free of any carbon-fluorine bond or it may be partially fluorinated, i.e. it may contain carbon-fluorine bonds. Should the hydrocarbon compound be free of any carbon-fluorine bond the end product of the process may be either a partially fluorinated compound or fully fluorinated compound.

Should the hydrocarbon compound contain carbon-fluorine bonds the end product of the process may be either a fully fluorinated compound or a partially fluorinated compound wherein at least one carbon-hydrogen bond has been replaced by a carbon-fluorine bond.

The term "alkane" is used herein to indicate a hydrocarbon containing only single carbon-carbon bonds.

According to an embodiment of the invention, the alkane comprising at least one carbon-hydrogen bond is selected among the straight-chain or branched-chain alkanes of formula (IA) or the cyclic alkanes of formula (IB) here below:

   (IA)

   (IB)

wherein:
X is selected from Cl, Br, I, —SO$_2$F, —SO$_2$Cl; preferably X is selected from Cl, —SO$_2$F, —SO$_2$Cl;
a is an integer≥1, preferably an integer from 1 to 30, more preferably from 2 to 20, still more preferably from 3 to 15, and even more preferably from 4 to 15;
b and c are integers≥0, such that (b+c)≤(2a+1);
a' is an integer from 3 to 20, preferably from 4 to 10;
b' and c' are integers≥0 such that (b'+c')≤(2a'−1).

Preferably the alkane comprising at least one carbon-hydrogen bond is liquid at the reaction temperature.

The hydrocarbon compound may alternatively be selected among straight-chain, branched-chain and cyclic ethers. The term "ether" is used herein to refer to organic compounds comprising at least one oxygen atom linking two hydrocarbon groups and thus it encompasses compounds comprising one or more than one etheric oxygen atom.

According to an embodiment of the invention, the ether comprising at least one carbon-hydrogen bond is selected among the straight-chain or branched-chain ethers of formula (IIA) or the cyclic ethers of formula (IIB) here below:

   (IIA)

   (IIB)

wherein:
X is selected from Cl, Br, I, —SO$_2$F, —SO$_2$Cl, preferably X is selected from —SO$_2$F or —SO$_2$Cl;
g is an integer≥1;
j and l are integers≥0, such that (j+1)≤(2g+1);
k and k' are integers≥1;
g' is an integer≥3, preferably from 3 to 20, more preferably from 4 to 10;
j' and l' are integers≥0 such that (j'+1')≤(2g'−1).

According to an embodiment the ether is selected among ethers obtained by addition of a hydrogen-containing alcohol, preferably a fluorine-free alcohol, to a perfluorinated or fluorinated olefin. The reaction is typically carried out by addition of the olefin to an alcohol, optionally in the presence of a polar aprotic solvent, in the presence of a base. Alternatively, the ether may be prepared by radical addition of a hydrogen-containing alcohol, preferably a fluorine-free alcohol, to a perfluorinatd or fluorinated olefin, followed by etherification of the partially fluorinated alcohol thus obtained according to methods well known in the art.

Non-limiting examples of suitable hydrogen-containing alcohols are C$_1$-C$_{18}$ monohydric or dihydric alcohols, preferably C$_1$-C$_{12}$ aliphatic alcohols such as methanol, ethanol, 1-propanol, 1-butanol, 1,2-ethanediol, 1,3-propanediol, 2,2-dimethyl-1,3-propanediol, diethylene glycol, triethylene glycol, tetraethylene glycol, glycerol, erythritol, xylitol, sorbitol.

Non-limiting examples of suitable perfluorinated or fluorinated olefins that may be used in the preparation of the ether compound are notably: C$_2$-C$_{18}$ fluoro and/or perfluoroolefins, such as tetrafluoroethylene (TFE), hexafluoropropylene (HFP), pentafluoropropylene, octafluorobutene, hexafluorobutadiene; perfluoroalkylvinyl ethers, such as perfluoromethylvinylether, perfluoroethylvinylether, perfluoropropylvinylether; and fluorodioxoles, such as perfluorodioxole or perfluoromethoxydioxole.

Notable examples of ethers deriving from the reaction of a fluorine-free alcohol with a fluorinated olefin are: HCF$_2$CF$_2$OCH$_2$CH$_2$OCF$_2$CF$_2$H, HCF$_2$CF$_2$OCH$_2$CH$_2$CH$_2$OCF$_2$CF$_2$H, CF$_3$CFHCF$_2$OCH$_2$CH$_2$OCF$_2$CFHCF$_3$, CF$_3$CFHCF$_2$OCH$_2$CH$_2$CH$_2$OCF$_2$CFHCF$_3$, HCF$_2$CF$_2$OCH$_2$[CH(OCF$_2$CF$_2$H)]$_2$CH$_2$OCF$_2$CF$_2$H, HCF$_2$CF$_2$OCH$_2$CH$_2$OCH$_2$CH$_2$OCF$_2$CF$_2$H, CF$_3$CFHCF$_2$OCH$_2$CH$_2$OCH$_2$CH$_2$OCF$_2$CFHCF$_3$.

According to another embodiment suitable ethers are fluorine-free ethers comprising recurring units R$^H$ chosen among the group consisting of:
(I') —CH$_2$O—;
(ii') —CH$_2$CH$_2$O—;
(iii') —CH$_2$CH$_2$CH$_2$O—;
(iv') —CH$_2$CH$_2$CH$_2$CH$_2$O—.

Notable examples are for instance poly(oxymethylene), poly(ethylene oxide), poly(propylene oxide), poly(tetrahydrofuran).

According to a further embodiment the ether is selected among those that comply with formula (IIC) here below:

   (IIC)

wherein:
R and R', equal or different from each other, are independently chosen among —$C_mH_{2m+1}$, —$C_qF_{2q+1}$, —$C_nF_{2n+1-h}H_h$, —$C_pF_{2p+1-h'}X_{h'}$, —$C_zF_{2z}OC_yF_{2y+1}$, —$C_uF_{2u-u'}H_{u'}OC_wF_{2w+1-w'}H_{w'}$, —$C_uF_{2u-u'}H_{u'}OC_yF_{2y+1}$ groups, with m, n, p, q, u, w, y, z being integers from 1 to 8, preferably from 1 to 7, h, h', u' and w' being integers≥1, chosen so that h≤2n+1, h'≤2p+1, u'≤2u, w'≤2w+1, X being a halogen atom chosen among Cl, Br, I, preferably Cl; with the proviso that at least one of R and R' in formula (IIC) is a —$C_mH_{2m+1}$, —$C_nF_{2n+1-h}H_h$ group or a —$C_uF_{2u-u'}H_{u'}OC_wF_{2w+1-w'}H_{w'}$ group, as defined above; —r is 0 or 1;

$R_f$ is a fluoropolyoxyalkylene chain comprising recurring units $R^F$, said recurring units being chosen among the group consisting of:
(i) —CFYO—, wherein Y is F or $CF_3$;
(ii) —$CF_2$CFYO—, wherein Y is F or $CF_3$;
(iii) —$CFYCF_2O$—, wherein Y is F or $CF_3$;
(iv) —$CF_2CF_2CF_2O$—;
(v) —$CH_2CF_2CF_2O$—;
(vi) —$CF_2CF_2CF_2CF_2O$—;
(vii) —$(CF_2)_k$—CFZ—O—, wherein k is an integer from 0 to 3 and Z is a group of general formula —$OR_TT_3$, wherein $R_T$ is a fluoropolyoxyalkylene chain comprising a number of recurring units from 0 to 10, said recurring units being chosen among the followings: —CFXO—, —$CF_2$CFYO—, —$CF_2CF_2CF_2O$—, —$CF_2CF_2CF_2CF_2O$—, with each of Y being independently F or $CF_3$, and $T_3$ is a $C_1$-$C_5$ perfluoroalkyl group, and mixtures thereof.

Preferably, in formula (IIC) above:
R and R', equal or different from each other, are independently chosen among —$C_mH_{2m+1}$, —$C_qF_{2q+1}$, —$C_nF_{2n+1-h}H_h$, —$C_uF_{2u-u'}H_{u'}OC_wF_{2w+1-w'}H_{w'}$, —$C_uF_{2u-u'}H_{u'}OC_yF_{2y+1}$ groups, with m, n, u, w, y being integers from 1 to 8, preferably from 1 to 7, h, u' and w' being integers≥1, chosen so that h≤2n+1, u'≤2u, w'≤2w+1, with the proviso that at least one of R and R' is a —$C_nF_{2n+1-h}H_h$ group, as defined above;
r is equal to 1;
$R_f$ has the same meaning as defined above.

More preferably in formula (IIC) above:
R and R', equal or different from each other, are independently chosen between —$C_qF_{2q+1}$ and —$C_nF_{2n+1-h}H_h$ groups, with q, n being integers from 1 to 8, h being integer≥1, chosen so that h≤2n+1, with the proviso that at least one of R and R' is a —$C_nF_{2n+1-h}H_h$ group, as defined above;

$R_f$ is chosen among the following:
(1) —$(CF_2O)_\alpha$—$(CF_2CF_2O)_\beta$—$(CF_2$—$(CF_2)_{z'}$—$CF_2O)_\gamma$, with α, β and γ being integers up to 100, preferably up to 50, and z' being an integer equal to 1 or 2, α≥0, β≥0, γ≥0 and α+β>0; preferably, each of α and β being >0 and β/α being comprised between 0.1 and 10;
(2) —$(C_3F_6O)_{\gamma'}$—$(C_2F_4O)_\beta$—$(CFYO)_t$—, with Y being, at each occurrence, independently selected among —F and —$CF_3$; β, γ' and t being integers up to 100, γ'>0, β≥0, t≥0; preferably, β and t>0, γ'/β being comprised between 0.2 and 5.0 and (γ'+β)/t being comprised between 5 and 50;
(3) —$(C_3F_6O)_{\gamma'}$—$(CFYO)_t$—, with Y being, at each occurrence, independently selected among —F and —$CF_3$; γ' and t being integers up to 100, γ'>0, t≥0, preferably t>0, γ'/t being comprised between 5 and 50.

Non limiting examples of ethers described by formula (IIC) include, but are not limited to, the following compounds and mixtures thereof: $HCF_2O(CF_2CF_2O)CF_2H$; $HCF_2O(CF_2CF_2O)_2CF_2H$; $HCF_2O(CF_2CF_2O)_2(CF_2O)_2CF_2H$; $HCF_2O(CF_2CF_2O)_3CF_2H$; $HCF_2O(CF_2CF_2O)_3(CF_2O)_2CF_2H$; $HCF_2O(CF_2CF_2O)_4CF_2H$; $HCF_2O(CF_2CF_2O)_3CF_2OCF_2H$; $HCF_2O(CF_2CF_2O)_4CF_2OCF_2H$; $CF_3O(CF_2CF_2O)_2CF_2H$; $CF_3O(CF_2CF_2O)_2(CF_2O)CF_2H$; $CF_3O(CF_2CF_2O)(CF_2O)_2CF_2H$; $CF_3O(CF_2CF_2O)_2(CF_2O)_2CF_2H$; $CF_3O(CF_2CF(CF_3)O)_2CF_2H$; $CF_3O(CF_2CF(CF_3)O)_3CF_2H$; $CF_3O(C_3F_6O)_2(CF(CF_3)O)CF_2H$; $CH_3O(CF_2CF_2O)_2CH_3$; $CH_3O(CF_2CF_2O)(CF_2O)(CF_2CF_2O)CH_3$; $CH_3O(CF_2CF_2O)_3CH_3$; $CH_3O(CF_2CF_2O)(CF_2O)_2(CF_2CF_2O)CH_3$; $C_2H_5OCF_2CF_2OC_2H_5$; $C_2H_5O(CF_2CF_2O)_2C_2H_5$; $C_2H_5O(CF_2CF_2O)_2CF_2H$.

In step B of the process, the hydrocarbon compound comprising at least one carbon-hydrogen bond is reacted with fluorine in the presence of a (per)haloolefin, as above defined, to obtain a hydrocarbon compound wherein at least one carbon-hydrogen bond has been replaced by a carbon-fluorine bond.

The process has been found to proceed in a stoichiometric manner whereby to each molecule of net fluorine $F_2$ fed to the reaction system corresponds the replacement of one carbon-hydrogen bond with one carbon-fluorine bond and the formation of hydrogen fluoride.

In the present specification the term "net" when used with reference to the amount of fluorine fed to the reaction system is used to indicate the amount of fed fluorine that has not been consumed in the reaction with the (per)haloolefin, i.e. the difference between the total amount of fluorine introduced into the reaction system and the stoichiometric amount reacted with the (per)haloolefin.

Generally fluorine is added to the reaction in an amount slightly higher than the stoichiometric amount necessary to convert a carbon-hydrogen bond in the hydrocarbon compound into a carbon-fluorine bond. Typically, the amount of net fluorine is 30 mol %, preferably 20 mol %, more preferably 10 mol % higher than said stoichiometric amount. Thus, the process typically proceeds by feeding to the reaction system from 1 to 1.3, preferably from 1 to 1.2, more preferably from 1 to 1.1, equivalents of fluorine per number of carbon-hydrogen bonds that have to be replaced in the hydrocarbon compound. Conversion of fluorine is generally greater than 90%.

According to one embodiment of the process, (per)haloolefins suitable for use in step B are those represented by the following formula:

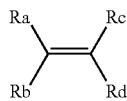

wherein $R_a$, $R_b$, $R_c$ and $R_d$ are each independently selected from the group consisting of F, Cl and hydrocarbon groups, possibly comprising one or more chlorine and/or fluorine atoms, optionally having one or more heteroatoms different from F and Cl, e.g. oxygen, possibly directly linked to the double bond. At least one of $R_a$, $R_b$, $R_c$ and $R_d$ is selected from fluorine or chlorine.

Preferably, $R_a$, $R_b$, $R_c$ and $R_d$ are each independently selected in the group consisting of F, Cl, $C_1$-$C_4$ perfluorocarbon groups, $C_1$-$C_4$ oxygen-containing perfluorocarbon groups, $C_1$-$C_4$ fluorochlorohydrocarbon groups, and $C_1$-$C_4$ oxygen-containing fluorochlorohydrocarbon groups. More preferably, at least three of $R_a$, $R_b$, $R_c$ and $R_d$ are selected from F, Cl and mixtures thereof.

As examples of such (per)haloolefins, mention may be made of tetrafluoroethylene (TFE), hexafluoropropylene (HFP) and its dimers and trimers, octafluorobutene, perfluoropentene, perfluorohexene, perfluoroheptene, perfluorooctene, perfluorocyclobutene, perfluorocyclopentene, perfluorocyclohexene, chlorotrifluoroethylene, dichlorodifluoroethylene, chloropentafluoropropene, perfluorobutadiene, perfluoromethylvinylether, perfluoroethylvinylether, perfluoropropylvinylether; $CF_3OCCl\!=\!CClF$, trichloroethylene, tetrachloroethylene, dichloroethylene isomers; and fluorodioxoles of formula:

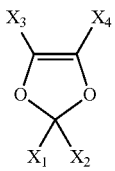

wherein $X_1$, $X_2$, $X_3$, and $X_4$, equal to or different from each other, are independently selected from F, $R_f$ and $OR_f$, wherein $R_f$ is a (per)fluorocarbon group, and wherein at least one of $X_3$, and $X_4$ is fluorine. Preferably the (per)haloolefin is selected from the group consisting of tetrafluoroethylene (TFE), hexafluoropropylene (HFP) and its dimers and trimers.

The amount of (per)haloolefin used in step B of the process is typically comprised in the range of 0.1 to 30 mol % with respect to the hydrogen atoms contained in the hydrocarbon compound. Preferably, said amount is comprised in the range of 0.5 to 20 mol % with respect to the hydrogen atoms contained in the hydrocarbon compound. More preferably, said amount is comprised in the range of 1 to 15 mol % with respect to the hydrogen atoms contained in the hydrocarbon compound.

The (per)haloolefin can be initially loaded in the reaction vessel or can be advantageously continuously fed in the required amount during the fluorination reaction.

Fluorine may be fed into the reactor as a pure gas or diluted with an inert gas, such as $N_2$, Ar and He.

Hydrogen fluoride is generated as a by-product during the fluorination reaction. Thus it may be preferable to add a hydrogen fluoride scavenger to the reaction system. Notable examples of hydrogen fluoride scavenger are for instance alkali metal fluorides such as NaF and KF.

The process is generally carried out in the liquid phase. The hydrocarbon compound may be allowed to react with fluorine in a non-solvent phase, provided that it is liquid in the reaction conditions, as well as diluted in a suitable solvent. Among suitable solvents, mention can be notably made of organic halogenated compounds, such as perfluoroalkanes, chlorofluoroalkanes, $CF_3OCFClCF_2Cl$, tertiary perfluorinated alkyl amines, perfluoropolyethers.

Surprisingly, the use of concentrated or pure reagents in the process does not lead to decomposition of the hydrocarbon compound, as the reaction exothermicity may be controlled.

As a matter of fact, the reaction temperature may be advantageously maintained in the range of $-100°$ C. to $+50°$ C.

Typically, fluorine and the (per)haloolefin, in separate feeds, are continuously added to the hydrocarbon at the given temperature of the process.

The process may proceed to the complete fluorination of the starting hydrocarbon compound. In such a case the end of the reaction can be advantageously detected by online analysis, by checking fluorine conversion, which typically suddenly drops to zero. Advantageously, no temperature increase, fluorine concentration increase or UV irradiation is required to perform the complete fluorination of the hydrocarbon compound.

Alternatively, the process may be controlled to reach only the partial substitution of the carbon-hydrogen bonds with carbon-fluorine bonds.

The process of the invention advantageously allows the controlled step-wise replacement of each carbon-hydrogen bond in the hydrocarbon compound with carbon-fluorine bond. The degree of substitution can be precisely controlled by feeding only the stoichiometric amount of net fluorine as discussed above.

The hydrogen substitution is not selective, in the sense that it is not generally possible to direct the substitution reaction onto a specific carbon-hydrogen bond in the hydrocarbon compound. Thus the product of the partial fluorination reaction will typically be a mixture of hydrocarbon compounds having the same number of carbon and, when present oxygen atoms and X substituents as defined above, but a different average degree of fluorine substitution. Said mixture of hydrocarbon compounds is characterised, with respect to the starting hydrocarbon compound, by a higher average number of carbon-fluorine bonds and a lower average number of carbon-hydrogen bonds. The difference between the number of carbon-fluorine bonds (or the number of carbon-hydrogen bonds) between the starting hydrocarbon compound and the final mixture of products is directly proportional to the amount of net fluorine fed to the system.

Without being bound by a particular theory the Applicant believes that the reaction for an alkene of formula (IA) or an ether of formula (IIA) might be represented as indicated in Scheme 1:

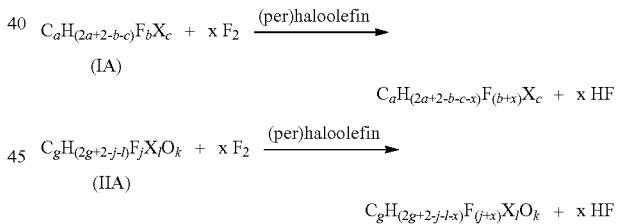

In Scheme 1, X, a, b, c, g, j, k and l are as defined above and x represents the moles of net fluorine fed to the reaction system.

The possibility to precisely control the degree of fluorine substitution in the hydrocarbon compound allows obtaining well defined mixtures of partially fluorinated compounds, starting from one single compound, whose physico-chemical properties, e.g. boiling temperature, may be fine tuned by changing the amount of fluorine fed during the process.

This feature of the inventive process may be particularly advantageous for the preparation of mixtures of partially fluorinated hydrocarbon compounds for use as solvents, e.g. in cleaning or coating applications, as refrigerants, as heat transfer fluids, as blowing agents.

Partially fluorinated hydrocarbon compounds, in particular ethers, are generally characterised by low ozone depletion potential, a boiling range suitable for solvent cleaning applications, and high solvency, i.e., the ability to readily dissolve or disperse organic and/or inorganic contaminants, such as water, hydrocarbon-based compounds, and fluorocarbon-based compounds, good thermal and chemical stability, short atmospheric lifetimes and low global warming potentials.

The Applicant has found that ethers derived from the reaction of a fluorine-free polyhydric alcohol with a perfluorinated olefin are particularly suitable starting hydrocarbon compounds to provide mixtures of compounds whose physico-chemical properties, in particular the boiling temperature, may be successfully fine tuned by means of the inventive process.

Fluorination of ethers derived from the reaction of a fluorine-free polyhydric alcohol with a perfluorinated olefin to obtain fully fluorinated products has been disclosed in SIEVERT, Allen, et al. Synthesis of perfluorinated ethers by an improved solution phase direct fluorination process. *J. Fluorine Chem.* 1991, vol. 53, p. 397-417.

Preferred starting hydrocarbon compounds for the preparation of mixtures are compounds which comply with formulas (IID) or (IIE) below:

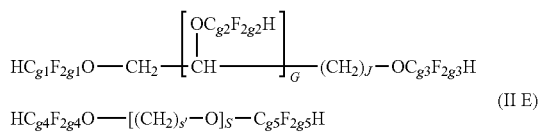

(II D)

(II E)

wherein:

each $g_1, g_2, \ldots g_i$ equal or different from each other, is independently chosen from integers from 2 to 10, preferably from 2 to 6;

G is an integer≥0 and up to 4; J is an integer≥0 and up to 6;

s' is an integer from 1 to 4; S is an integer from 2 to 5.

Preferably, in formula (IID) above, each $g_i$, equal or different from each other, is independently 2 or 3; G is 0 or 1 and J is an integer from 1 to 4.

Preferably in formula (IIE) above, each $g_i$, equal or different from each other, is independently 2 or 3; s' and S are independently from each other 1, 2 or 3. More preferably s' is 2 or 3 and S is 1, 2 or 3.

The mixtures obtained by partial fluorination according to the inventive process of a hydrocarbon compound represented by formulas (IID) or (IIE) as detailed above, can be represented by the following general formulas (IID1) or (IIE1) respectively:

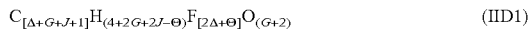

(IID1)

wherein:

$\Delta = g1 + g3 + G \cdot g2$ and $\Theta$ is a rational number that can take any value from 0 to (4+2G+2J), extremes excluded;

(IIE1)

wherein
$\Delta' = g4 + g5$; and
$\Theta'$ is a rational number that can take any value from 0 to (2+2s'·S), extremes excluded.

The value of $\Theta$ or $\Theta'$ is proportional to the amount of fluorine reacted with the starting hydrocarbon compound. By varying $\Theta$, or $\Theta'$ it is possible to change the physico-chemical properties of the mixture. For instance it is possible to vary the boiling temperature of the mixture over a wide range which is comprised between the boiling temperature of the fully fluorinated hydrocarbon compound, when $\Theta=4+2G+2J$ in formula (IID1) or $\Theta'=2+2s'\cdot S$ in formula (IIE1)) and that of the starting material, when $\Theta=0$ or $\Theta'=0$.

Accordingly a further object of the invention is a composition comprising at least two compounds selected either from the group of compounds having formula (IID1) said at least two compounds characterised by the same values of $\Delta$, G and J and each one having a different value of $\Theta$ or at least two compounds selected from the group of compounds having formula (IIE1) said at least two compounds characterised by the same values of $\Delta'$, s' and S and each one having a different value of $\Theta'$.

Said compositions advantageously have boiling temperatures comprised between 20 and 350° C., typically between 50 and 250° C., more typically between 75 and 200° C., and even more typically between 70 and 180° C.

In a first embodiment the composition comprises at least two compounds selected from the group of compounds having formula (IIE1) wherein g4=g5=2, s'=2 and S=1. In a preferred aspect of this first embodiment the composition has a boiling temperature between 75 and 135° C., preferably between 80 and 130° C.

In a second embodiment the composition comprises at least two compounds selected from the group of compounds having formula (IIE1) wherein g4=g5=2, s'=2 and S=2. In a preferred aspect of this second embodiment the composition has a boiling temperature between 110 and 200° C., preferably between 140 and 190° C.

In a third embodiment the composition comprises at least two compounds selected from the group of compounds having formula (IIE1) wherein g4=g5=2, s'=3 and S=1. In a preferred aspect of this third embodiment the composition has a boiling temperature between 120 and 180° C., preferably between 125 and 170° C.

In a fourth embodiment the composition comprises at least two compounds selected from the group of compounds having formula (IIE1) wherein g4=g5=3, s'=2 and S=1. In a preferred aspect of this fourth embodiment the composition has a boiling temperature between 110 and 170° C., preferably between 120 and 160° C.

Compositions having boiling temperatures falling within said ranges are suitable for applications such as: solvents for e.g. cleaning or coating applications; heat transfer fluids; blowing agents.

The invention will be now described in more detail with reference to the following examples, whose purpose is merely illustrative and not intended to limit the scope of the invention. Should the disclosure of any patents, patent applications, and publications which are incorporated herein by reference conflict with the description of the present application to the extent that it may render a term unclear, the present description shall take precedence.

EXAMPLES

Example 1

Synthesis of a Mixture having Raw Formula $C_6H_4F_{10}O_2$

In a 250 ml stainless steel reactor a mixture constituted by 20.3 g (0.077 mol) of $HCF_2CF_2OCH_2CH_2OCF_2CF_2H$ ($C_6H_6F_8O_2$) and 114.2 g of $CF_3OCFClCF_2Cl$ as solvent were charged. The temperature was set at −50° C. and fluorine (1.65 Nl/h in 3.0 Nl/h of helium) and hexafluoropropylene (0.15 Nl/h in 1.5 Nl/h of helium) were fed under vigorous stirring, by two inlet pipes. After 150 minutes the feeding of the gaseous reagents (corresponding to 0.167 mol of net fluorine) was stopped and any residual gas purged away by a helium flow; the crude mixture was distilled providing a mixture of ethers having the raw formula $C_6H_4F_{10}O_2$ (as determined by NMR analysis) and a boiling temperature of 125° C.

Example 2

Synthesis of a Mixture having Raw Formula $C_6H_{2.2}F_{1.8}O_2$

The same procedure described in Example 1 (20.1 g, 0.077 mol of starting ether and 101.3 g of solvent) was repeated but feeding fluorine and hexafluoropropylene for 4 hours and 35 minutes (corresponding to 0.307 mol of net fluorine). The crude mixture was distilled providing a mixture of ethers having the raw formula $C_6H_{2.2}F_{11.8}O_2$ (as determined by NMR analysis) and a boiling temperature of 100° C.

Example 3

Synthesis of a Mixture having Raw Formula $C_6HF_{13}O_2$

The same procedure described in Example 1 (20.2 g, 0.077 mol, of starting ether and 105.7 g of solvent) was repeated but feeding fluorine and hexafluoropropylene for 6 hours and 15 minutes (corresponding to 0.418 mol of net fluorine). The resulting mixture had the raw formula $C_6HF_{13}O_2$ and a boiling temperature of 80° C.

Example 4

Perfluorination of $CF_2HO(CF2O)_m(CF_2CF_2O)_n CF_2H$ 59.8 g (0.127 mol) of a compound having generic formula $CF_2HO(CF_2O)_m(CF_2CF_2O)_n CF_2H$, with m and n values giving a molecular weight of 472 g/mol were charged in a 250 ml stainless steel reactor kept at 5° C. and under vigorous stirring. Fluorine (1.60 Nl/h in 3.0 Nl/h of helium) and hexafluoropropylene (0.10 Nl/h in 1.5 Nl/h of helium) were fed by two inlet pipes; after 4 hours the addition of the gaseous reagents (corresponding to 0.268 mol of net fluorine) was stopped and the residual gases vented away. The crude mixture was analyzed by NMR analysis: 10 ppm of residual hydrogen atoms (vs. 4200 ppm in the starting compound) with a hydrogen conversion higher than 99%.

Example 5

Comparative

The reaction described in Example 4 was repeated without the addition of hexafluoropropylene. Hydrogen conversion resulted below 5%.

Example 6

Synthesis of a Mixture having Raw Formula $C_7H_{7.2}F_{8.8}O_2$ 57.9 g (0.210 mol) of $HCF_2CF_2OCH_2CH_2CH_2OCF_2CF_2H$ ($C_7H_8F_8O_2$) were charged in a 250 ml stainless steel reactor cooled at −30° C. Fluorine (1.65 Nl/h in 3.0 Nl/h of helium) and hexafluoropropylene (0.15 Nl/h in 1.5 Nl/h of helium) were fed under vigorous stirring. After 2 hours and 50 minutes the flow of gaseous reagents was stopped (corresponding to 0.190 mol of net fluorine) and the residual gases purged away by helium. The crude mixture was washed with a saturated $NaHCO_3$ water solution obtaining a mixture of ethers having the raw formula $C_7H_{7.2}F_{8.8}O_2$ (as determined by NMR analysis). The boiling point of the mixture was 162° C.

Example 7

Synthesis of a Mixture having Raw Formula $C_7H_6F_{10}O_2$

Following the same procedure described in Example 6 (49.9 g, 0.181 mol, of starting ether) fluorine and hexafluoropropylene were fed for 6 hours and 15 minutes (corresponding to 0.401 mol of net fluorine). The resulting mixture, after basic wash, had the raw formula $C_7H_6F_{10}O_2$ and a boiling temperature of 152° C.

Example 8

Synthesis of a Mixture having Raw Formula $C_8H_{4.5}F_{13.5}O_2$ 45.2 g (0.125 mol) of $CF_3CFHCF_2OCH_2CH_2OCF_2CFHCF_3$ ($C_8H_6F_{12}O_2$) were charged in a 250 ml stainless steel reactor at 0° C. Fluorine (1.65 Nl/h in 3.0 Nl/h of helium) and hexafluoropropylene (0.15 Nl/h in 1.5 Nl/h of helium) were fed under vigorous stirring. After 3 hours and 10 minutes the flow of gaseous reagents was stopped (corresponding to 0.212 mol of net fluorine) and the residual gases purged away. The crude mixture was washed with a saturated water solution of $NaHCO_3$ obtaining a mixture having the raw formula $C_8H_{4.5}F_{13.5}O_2$ (as determined by NMR analysis) and a boiling temperature of 146° C.

Possible modifications and/or additions may be made by those skilled in the art to the hereinabove disclosed and illustrated embodiment while remaining within the scope of the following claims.

The invention claimed is:
1. A composition comprising either
   a) at least two compounds selected from the group consisting of compounds having formula (II D1) $C_{[A+G+J+1]}H_{(4+2G+2J-\Theta)}F_{[2A+\Theta]}O_{(G+2)}$, wherein said at least two compounds have the same values of A, G and J and each one having a different value of $\Theta$ wherein $0 \le \Theta \le (4+2G+2J)$ or
   b) at least two compounds selected from the group consisting of compounds having formula (II E1) $C_{[A'+s'S]}H_{(2+2s'S-\Theta')}F_{[2A'+\Theta']}O_{(S+1)}$, wherein said at least two compounds have the same values of $\Delta'$, s' and S and each one having a different value of $\Theta'$ wherein $0 \le \Theta' \le (2+2s' \cdot S)$; and
   wherein
      $\Delta = g1 + g3 + G \cdot g2$ and $\Theta$ is a rational number that can take any value from 0 to $(4+2G+2J)$, extremes excluded;
      $\Delta' = g4 + g5$;
      $\Theta'$ is a rational number that can take any value from 0 to $(2+2s' \cdot S)$, extremes excluded; and
      each $g_1, g_2, \ldots g_i$ equal or different from each other, is independently selected from integers from 2 to 10.

2. The composition according to claim 1 wherein
when the at least two compounds are selected from the group consisting of compounds having formula (II D1) each $g_i$, equal or different from each other, is independently 2 or 3; G is 0 or 1 and J is an integer from 1 to 4 or
when the at least two compounds are selected from the group of compounds having formula (II E1) each $g_i$, equal or different from each other, is independently 2 or 3; and s' and S independently of each other are 1, 2 or 3.

3. The composition according to claim 1 having a boiling temperature in the range from 20 to 350° C.

4. The composition according to claim 1 wherein the at least two compounds are selected from the group consisting of compounds having formula (II E1) wherein each $g_i$, equal or different from each other, is independently 2 or 3; and s' and S independently of each other are 1, 2 or 3; said composition having a boiling temperature in the range from 75 to 200° C.

5. A method for cleaning or coating comprising the step of using a composition of claim 1 as solvent.

6. A heat transfer fluid comprising the composition of claim 1.

7. A process for making a composition of claim 1, the process comprising:
reacting an ether with fluorine in the presence of at least one (per)haloolefin comprising at least one carbon-carbon double bond and having at least one fluorine or chlorine atom on either one of the carbon atoms of said double bond, said (per)haloolefin being present in an amount of 0.1 to 30 mol % with respect to the hydrogen atoms contained in said hydrocarbon compound, to obtain a fluorinated compound wherein at least one carbon-hydrogen bond has been replaced by a carbon-fluorine bond, wherein the ether complies with formula (II D) or (II E):

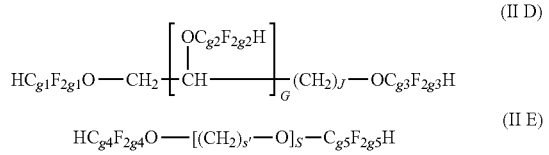

wherein:
each $g_1, g_2, \ldots g_i$ equal or different from each other, is independently selected from integers from 2 to 10;
G is an integer $\geq 0$ and up to 4; J is an integer $\geq 0$ and up to 6;
s' is an integer from 1 to 4; S is an integer from 2 to 5, and
wherein the amount of fluorine is less than the amount required to replace all the carbon-hydrogen bonds in the hydrocarbon compound with carbon-fluorine bonds.

8. The process according to claim 7 wherein said alkane is selected from the group consisting of the straight-chain or branched-chain alkanes of formula (IA) $C_aH_{(2a+2-b-c)}F_bX_c$ or the cyclic alkanes of formula (IB) $C_{a'}H_{(2a'-b'-c')}F_{b'}X_{c'}$ wherein: X is selected from Cl, Br, I, —SO$_2$F, —SO$_2$Cl; a is an integer $\geq 1$, b and c are integers $\geq 0$, wherein (b+c)$\leq$(2a+1); a' is an integer from 3 to 20; b' and c' are integers $\geq 0$ wherein (b'+c')$\leq$(2a'-1).

9. The process according to claim 7, wherein said ether is selected from the group consiting of the straight-chain or branched-chain ethers of formula (IIA) $C_gH_{(2g+2-j-1)}F_jX_lO_k$ or the cyclic ethers of formula (IIB) $C_gH_{(2g'-j'-1')}F_jX_lO_{k'}$, wherein: X is selected from Cl, Br, I, —SO$_2$F, —SO$_2$Cl; g is an integer $\geq 1$; j and l are integers $\geq 0$, wherein (j+1)$\leq$(2g+1); k and k' are integers $\geq 1$; g' is an integer $\geq 3$, j' and l' are integers $\geq 0$ wherein (j'+1')$\leq$(2g'-1).

10. The process according to claim 9, wherein the ether is selected from the group consisting of those that comply with formula (II C) RO—(R$_f$)$_r$—R', wherein:
R and R', equal or different from each other, are independently selected from the group consisting of —C$_m$H$_{2m+1}$, —C$_q$F$_{2q+1}$, —C$_n$F$_{2n+1-h}$H$_h$, —C$_p$F$_{2p+1-h'}$X$_{h'}$, —C$_z$F$_{2z}$OC$_y$F$_{2y+1}$, —C$_u$F$_{2u-u'}$H$_{u'}$OC$_w$F$_{2w+1-w'}$H$_{w'}$, and —C$_u$F$_{2u-u'}$H$_{u'}$OC$_y$F$_{2y+1}$ groups, wherein m, n, p, q, u, w, y, z being integers from 1 to 8, h, h', u' and w' being integers $\geq 1$, wherein h$\leq$2n+1, h'$\leq$2p+1, u'$\leq$2u, w'$\leq$2w+1, X being a halogen atom selected from the group consisting of Cl, Br, and I; wherein at least one of R and R' in formula (II C) is a —C$_m$H$_{2m+1}$, —C$_n$F$_{2n+1-h}$H$_h$ group or a —C$_u$F$_{2u-u'}$H$_{u'}$OC$_w$F$_{2w+1-w'}$H$_{w'}$ group, as defined above;
r is 0 or 1;
R$_f$ is a fluoropolyoxyalkylene chain comprising recurring units R$^F$, said recurring units are selected from the group consisting of:
(i) —CFYO—, wherein Y is F or CF$_3$;
(ii) —CF$_2$CFYO—, wherein Y is F or CF$_3$,
(iii) —CFYCF$_2$O—, wherein Y is F or CF$_3$,
(iv) —CF$_2$CF$_2$CF$_2$O—;
(v) —CH$_2$CF$_2$CF$_2$O—;
(vi) —CF$_2$CF$_2$CF$_2$CF$_2$O—; and
(vii) —(CF$_2$)$_k$—CFZ—O—, wherein k is an integer from 0 to 3 and Z is a group of general formula —OR$_T$T$_3$, wherein R$_T$ is a fluoropolyoxyalkylene chain comprising a number of recurring units from 0 to 10, said recurring units being selected from the group consisting of —CFXO—, —CF$_2$CFYO—, —CF$_2$CF$_2$CF$_2$O—, —CF$_2$CF$_2$CF$_2$CF$_2$O—, and mixtures thereof, wherein each of Y being independently F or CF$_3$, and T$_3$ is a C$_1$-C$_5$ perfluoroalkyl group.

11. The process according to claim 9, wherein the ether is selected from ethers obtained by the addition of a hydrogen-containing alcohol, to a perfluorinated or fluorinated olefin.

12. The process according to claim 11, wherein the ether complies with formula (II D) or (II E):

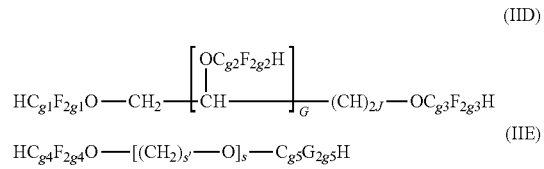

wherein:
each $g_1, g_2, \ldots g_i$ equal or different from each other, is independently selected from integers from 2 to 10;
G is an integer $\geq 0$ and up to 4; J is an integer $\geq 0$ and up to 6;
s' is an integer from 1 to 4; S is an integer from 2 to 5.

13. The process according to claim 12 wherein the amount of fluorine is less than the amount required to replace all the carbon-hydrogen bonds in the hydrocarbon compound with carbon-fluorine bonds, said process providing a mixture of compounds represented by the general formula (II D1):

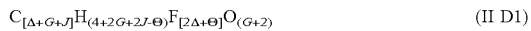   (II D1)

wherein:
$\Delta = g1 + g3 + G \cdot g2$ and $\Theta$ is a rational number that can take any value from 0 to $(4+2G+2J)$, extremes excluded; or by the general formula (II E1):

   (II E1)

wherein
$\Delta' = g4 + g5$; and
$\Theta'$ is a rational number that can take any value from 0 to $(2+2' \cdot S)$, extremes excluded; and wherein each $g_1$, $g_2$, ... $g_i$ equal or different from each other, is independently selected from integers from 2 to 10.

14. The process according to claim 7, wherein the (per) haloolefin complies with the following formula:

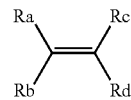

wherein $R_a$, $R_b$, $R_c$ and $R_d$ are each independently selected in the group consisting of F, Cl and hydrocarbon groups, optionally comprising one or more chlorine and/or fluorine atoms, optionally having one or more heteroatoms different from fluorine and chlorine, optionally directly linked to the double bond.

15. The process according to claim 7, wherein the amount of fluorine is 1 to 1.3 equivalents of fluorine per number of carbon-hydrogen bonds that have to be replaced in the hydrocarbon compound.

* * * * *